United States Patent
Fay et al.

(10) Patent No.: US 9,750,564 B2
(45) Date of Patent: Sep. 5, 2017

(54) FLEXIBLE CATHETER FOR HIGH-FREQUENCY THERAPY OF BIOLOGICAL TISSUE AND METHOD OF USING SAME

(75) Inventors: Markus Fay, Teltow (DE); Wolfgang Kühne, Schönfliess (DE)

(73) Assignee: CELON AG MEDICAL INSTRUMENTS (DE)

( * ) Notice: Subject to any disclaimer, the term of this patent is extended or adjusted under 35 U.S.C. 154(b) by 1500 days.

(21) Appl. No.: 12/085,720

(22) PCT Filed: Oct. 4, 2007

(86) PCT No.: PCT/EP2007/060556
§ 371 (c)(1),
(2), (4) Date: May 28, 2008

(87) PCT Pub. No.: WO2008/040788
PCT Pub. Date: Apr. 10, 2008

(65) Prior Publication Data
US 2009/0156981 A1    Jun. 18, 2009

(30) Foreign Application Priority Data
Oct. 4, 2006    (DE) .................... 10 2006 047 366

(51) Int. Cl.
*A61B 18/14*    (2006.01)
*A61B 18/00*    (2006.01)

(52) U.S. Cl.
CPC  *A61B 18/1492* (2013.01); *A61B 2018/00345* (2013.01); *A61B 2018/00482* (2013.01); *A61B 2018/00559* (2013.01)

(58) Field of Classification Search
CPC ...... A61B 18/1492; A61B 2018/00345; A61B 2018/00482; A61B 2018/00559
USPC ................................................ 606/41, 45–50
See application file for complete search history.

(56) References Cited

U.S. PATENT DOCUMENTS

| | | | |
|---|---|---|---|
| 5,423,878 A | | 6/1995 | Franz |
| 5,437,664 A | * | 8/1995 | Cohen et al. .................... 606/42 |
| 5,536,248 A | * | 7/1996 | Weaver et al. ............... 604/506 |
| 5,545,161 A | | 8/1996 | Imran |
| 5,695,495 A | | 12/1997 | Ellman et al. |
| 5,782,760 A | * | 7/1998 | Schaer .......................... 600/381 |
| 6,156,032 A | * | 12/2000 | Lennox ........................... 606/41 |
| 6,736,808 B1 | | 5/2004 | Motamedi et al. |
| 6,818,000 B2 | * | 11/2004 | Muller et al. ................... 606/41 |

(Continued)

FOREIGN PATENT DOCUMENTS

| | | |
|---|---|---|
| WO | 96/37146 A1 | 11/1996 |
| WO | 2006/017754 A1 | 2/2006 |

*Primary Examiner* — Michael Peffley
*Assistant Examiner* — Samantha Good
(74) *Attorney, Agent, or Firm* — Ware, Fressola, Maguire & Barber LLP

(57) ABSTRACT

A catheter for the high-frequency therapy of body lumens has a flexible shaft tube of preferably biocompatible plastic material, which is connected to a distal end piece in the region of the distal end of the catheter. A proximal part of the distal end piece, that projects into the distal part of the shaft tube, forms a damping connection to the distal end of the shaft tube, which is secured by a distal electrode which is drawn on to the external peripheral surface of the shaft tube, by the distal electrode exerting a radially inwardly acting clamping force on the damping connection.

39 Claims, 4 Drawing Sheets

(56) References Cited

U.S. PATENT DOCUMENTS

2002/0148476 A1* 10/2002 Farley et al. ............... 128/898
2004/0116793 A1    6/2004 Taimisto et al.
2004/0162555 A1*  8/2004 Farley et al. ............... 606/45
2005/0267467 A1* 12/2005 Paul et al. ................. 606/41

* cited by examiner

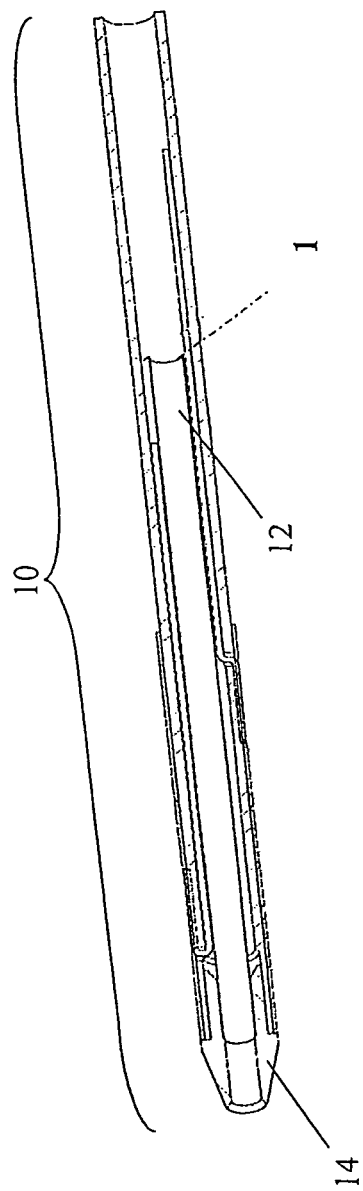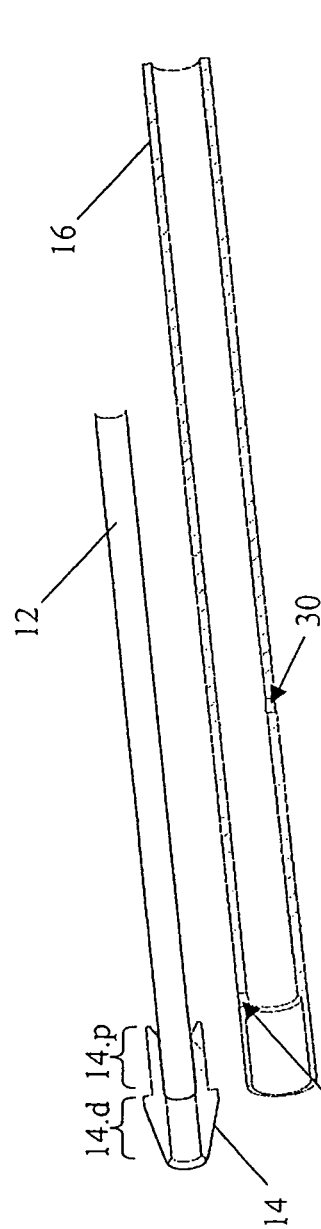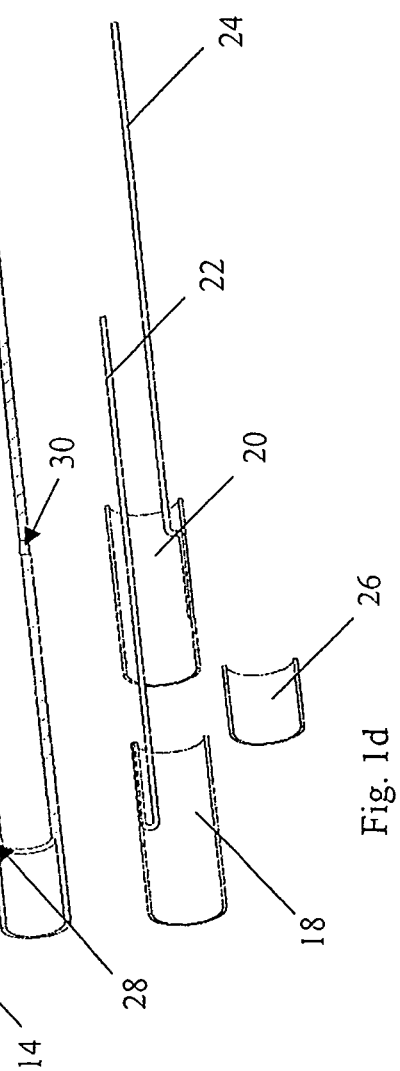

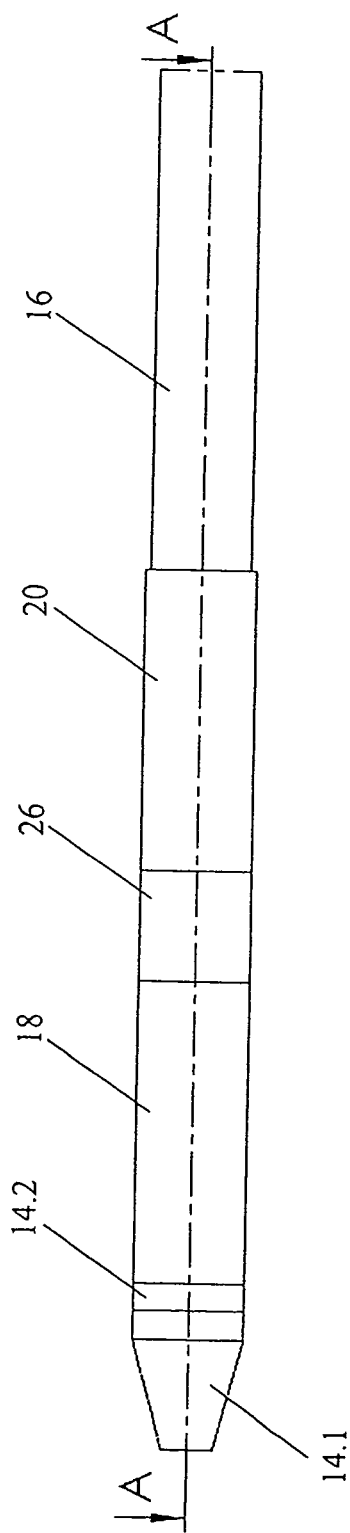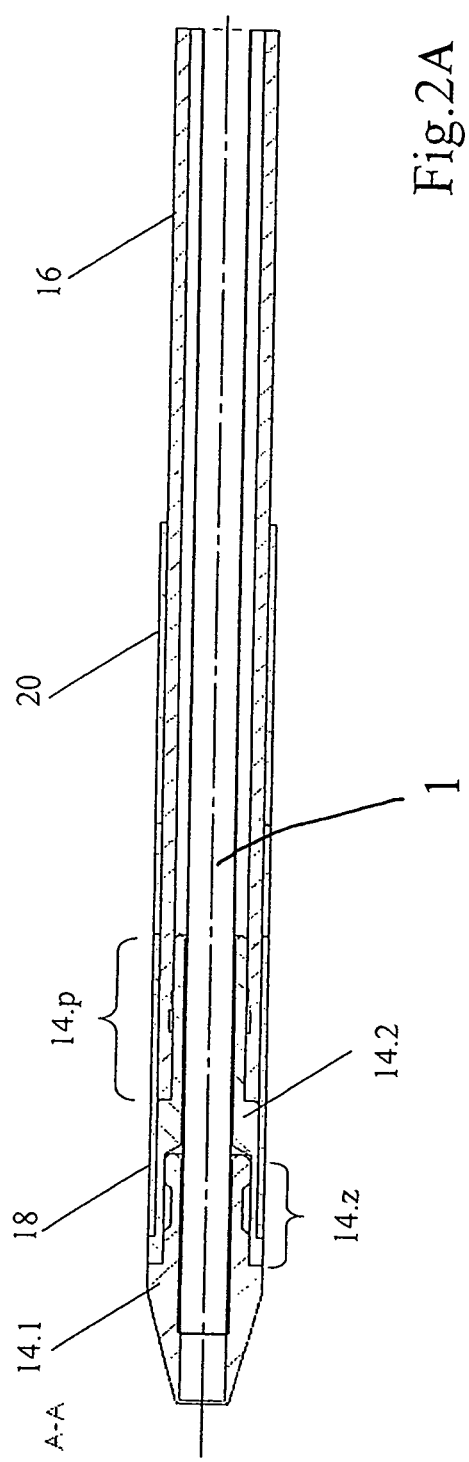

FLEXIBLE CATHETER FOR HIGH-FREQUENCY THERAPY OF BIOLOGICAL TISSUE AND METHOD OF USING SAME

BACKGROUND OF THE INVENTION

1. Technical Field

The invention concerns a flexible catheter of preferably biocompatible plastic material comprising at least one electrode disposed at the distal end of the catheter for high-frequency therapy of biological tissue.

2. Description of the Background Art

Catheters for high-frequency therapy are basically known. During a high-frequency therapy procedure, the application of a high-frequency ac voltage between two electrodes causes an electric current to be produced in the body tissue between the electrodes, and the result of that electric current is an increase in temperature of the body tissue surrounding the electrodes. With a type of catheter in accordance with this application the electrodes are in electrically conductive relationship with the body tissue after being introduced into a body lumen (for example blood vessel or bile duct) of the patient. The alternating current applied by way of the electrodes is converted into Joulean heat by the ohmic resistance of the body tissue. At temperatures between 50° C. and 100° C., denaturing of the body-specific proteins occurs (coagulation) and as a consequence that involves the area of tissue concerned shrinking or dying off. By virtue of the high current density at the active electrodes the increase in temperature occurs predominantly in the region of those electrodes so that a locally limited thermal use is possible.

U.S. Pat. No. 5,782,760 and WO 2006/017754 A1 disclose catheters for high-frequency therapy of hollow organs.

Catheters for high-frequency therapy of or in hollow organs of the general kind set forth comprise:
- a flexible shaft tube of biocompatible plastic material, the internal peripheral surface of which encloses a lumen and the external peripheral surface of which represents the external periphery of the catheter shaft,
- a distal shaft portion having at least one electrode for the delivery of high-frequency alternating current to the tissue surrounding the catheter in the treatment situation,
- an electric line which is electrically conductingly connected to the electrode and which extends to the proximal end of the catheter, and
- a distal end piece fixed to the distal end of the flexible shaft tube.

SUMMARY OF THE INVENTION

Now the object of the present invention is to provide a catheter for high-frequency therapy in body lumens which are in part fluid-filled, which affords reliable functioning and a simple structure.

In accordance with the invention that object is attained by a catheter of the kind set forth in the opening part of this specification, having a distal end piece which projects with a proximal end portion into the lumen of the flexible shaft tube and there forms a clamping connection to the distal end of the shaft tube. The clamping connection is secured in that case by a sleeve in the form of a hollow cylinder which exerts a radially acting damping force on the clamping connection. Preferably for that purpose the sleeve is pulled on to the external peripheral surface of the flexible shaft tube in order to secure the clamping connection from the outside, by a radially inwardly acting force. In the event that the end piece has a central through bore, the sleeve in a further embodiment can also be pushed into the end piece and can thus secure the clamping connection from the inside by a radially outwardly acting force.

If the sleeve is pulled on to the flexible shaft tube then in accordance with a particularly preferred embodiment it can be in the form of an electrode.

Preferably the distal end piece has a proximal part with at least one change in cross-section on the external peripheral surface, which makes it more difficult to displace the end piece in the axial direction. The change in cross-section is preferably in the form of a radially outwardly protruding projection.

In accordance with its two main configurations, the catheter shaft is either closed at the distal end or it has an opening at the distal end of the shaft. In this main configuration which is referred to as the second one, the catheter shaft has an internal lumen—which is continuous from the distal end to the proximal end of the catheter—and which is preferably of such a configuration that a guide wire can pass into the lumen through the proximal opening and can issue again through the distal opening. If in accordance with the main configuration referred to as the first configuration, the catheter is closed at the distal end, then in accordance with a further design configuration it can have a cooling system which is connected to a proximal feed and discharge flow of a coolant and which circulates within the lumen of the catheter, that is dosed to the distal end.

The electrode preferably comprises a conducting biocompatible material. In a particularly preferred variant at least the distal electrode consists entirely or in parts of surgical high-quality steel. In accordance with further configurations it can also be made from platinum, titanium, iridium or gold. In a preferred variant at least the distal electrode is of a wall thickness of 0.1 mm and along the axis of the catheter, is of an extent of about 5.4 mm. In a further preferred embodiment the catheter has two ring electrodes of which the proximal electrode and the distal electrode are identical in terms of dimensions.

In both main variants, preferably a further electrode is pulled on to the shaft tube, as the proximal electrode. It can comprise the same material and can be constructed in the same fashion as the distal electrode. A more flexible design configuration for the electrode is however also possible, comprising for example braided wire, cuff-like segments, in the form of a helical coil or the like, in order to ensure flexibility of the overall catheter shaft or to increase same in comparison with a shaft tube having a plurality of rigid electrodes.

In accordance with further variants three or more electrodes are pulled on to the shaft tube. In any bipolar or multipolar configuration of the catheter, preferably an insulator is pulled on to the shaft tube between the electrodes, wherein in a preferred variant the insulator is of a wall thickness which is also 0.1 mm and is of an extent of about 10% of the axial active length of the electrodes along the axis of the catheter shaft. Preferably that insulator is formed from PEEK.

The electrodes are electrically conductingly connected by way of lines to a connecting terminal for a high-frequency generator, the connecting terminal being arranged at the proximal end of the catheter shaft. In a preferred embodiment the lines which preferably extend embedded in the peripheral surface of the shaft tube comprise copper and are of a diameter of preferably 0.15 mm.

If in accordance with a further embodiment the lines do not extend embedded in the peripheral surface but extend along the internal peripheral surface of the shaft tube, it is necessary in particular in the variant of the catheter with an open distal end that the lines are insulated with respect to the entering fluid.

If the catheter is intended to be pulled on to a guide wire, it is also necessary for the lines to be protected from mechanical loadings due to the guide wire. Particularly for those two cases, a further embodiment provides that a plastic hose is drawn into the lumen of the flexible shaft tube.

In accordance with this variant the lines extend between the external peripheral surface of the hose and the internal peripheral surface of the shaft tube. Preferably the outside diameter of the plastic hose and the inside diameter of the shaft tube are so selected that, after the plastic hose has been drawn into the lumen of the shaft tube, it is fluid-tightly connected to the periphery of the shaft tube so that no fluid can penetrate into the intermediate space between the shaft tube and the plastic hose. A fluid-tight arrangement can also be achieved by glueing or welding. In order to avoid a possible mutual electrical contact between the lines and thus a short-circuit, the lines between the electrode and the proximal end of the catheter can also be individually covered with an electrically insulating material. The connection between the plastic hose and the shaft tube does not then necessarily have to be fluid-tight.

At the distal end of the shaft tube the lines are preferably connected to the electrodes by a clamping contacting arrangement. In that case the lines are clamped between the electrode and the shaft tube by the radially inwardly acting clamping force of the electrodes so that an electrical contact is afforded. In order to guide the electric lines from the intermediate space between the internal peripheral surface of the shaft tube and the external peripheral surface of the plastic hose through the periphery of the shaft tube on to the external peripheral surface of the shaft tube, radially oriented passage means are provided in the peripheral surface of the shaft tube. The distal end portions of the lines are passed 15 through those passage means and bent in such a way that they extend in the longitudinal direction of the shaft tube between the outer peripheral surface of the shaft tube and the respective electrode, and are clamped there.

The plastic hose which is drawn into the lumen of the shaft tube is made from a biocompatible polymer, more specifically preferably polyimide (PI). It is preferably of an inside diameter which is suitable for accommodating a guide wire of an outside diameter of 0.025 inch or 0.035 inch.

In a preferred embodiment the plastic hose is of an inside diameter of 0.65 to 1.0 mm, in a particularly preferred embodiment the inside diameter 25 is 0.81 mm. The internal peripheral surface of the plastic hose can be provided with an anti-adhesion coating. In a corresponding fashion, in accordance with the above-described variant of a shaft tube without a plastic hose pulled thereinto, the internal peripheral surface of the shaft tube can also be provided with an anti-adhesion coating.

In a preferred embodiment the flexible shaft tube is formed from polyetheretherketone (PEEK) and is preferably of an outside diameter of less than 5 mm and particularly preferably less than or equal to 1.8 mm. The external peripheral surface of the shaft tube can also be provided with an anti-adhesion coating.

In accordance with a further embodiment, the distal end piece which is normally made in one piece can be divided into two and can comprise a proximal and a distal sub-piece, wherein the proximal and the distal sub-pieces of the end piece are connected together by way of a force-locking connection, a positively locking connection or a connection involving intimate joining of the materials concerned. Preferably a distal portion of the proximal sub-piece of the end piece surrounds the proximal portion of the distal sub-piece, but a reversed arrangement of the two sub-pieces is also provided in accordance with a further embodiment.

If the end piece is divided into two the sleeve preferably encloses both sub-pieces of the distal end piece at least over a partial length where a distal portion of the proximal sub-piece of the end piece surrounds a proximal portion of the distal sub-piece.

Suitable recesses on the external peripheral surface of the proximal portion of the distal sub-piece of the end piece can serve as an adhesive reservoir, by means of which a secure adhesive join is afforded between the distal and the proximal sub-pieces.

In a further variant a distal part of the end piece is in the form of a pointed tip. In accordance with the main variant of the catheter with a distal opening, the pointed tip is correspondingly provided with an axial through bore forming a distal mouth opening of the lumen. The pointed tip preferably comprises polyphenylsulfone (PPSU) or polyetheretherketone (PEEK) and can optionally also be provided with an anti-adhesion coating.

The maximum diameter of the pointed tip which is preferably of a frustoconical configuration is preferably the same diameter as the outside diameter of the distal ring electrode. The conical outside surface of the pointed tip is of such a configuration that the outside diameter of the pointed tip tapers at an angle of 5 to 85 degrees, particularly preferably 15 degrees (measured between the gradient of the peripheral surface of the cone and a line parallel to the longitudinal axis of the catheter) towards the distal end of the catheter. In a particularly preferred variant the distal mouth opening of the pointed tip enlarges from a point between the distal and proximal ends of the pointed tip to the distal end of the catheter. That serves inter alia to provide that the guide wire can be more easily introduced. The incline resulting from that enlargement of the mouth opening preferably extends at an angle of between 20 and 45 degrees measured with respect to the longitudinal axis of the catheter.

Depending on the respective embodiment involved, the distal end piece at its distal end has a mouth diameter of 0.65 to 2 mm. The distal part, of a frustoconical configuration, of the distal end piece serves in particular to simplify the intraluminal advance of the catheter.

In a further embodiment the electrode can also be designed with a head-shaped, conical, trocar-shaped or spherical end face and thus at the same time can form the distal end piece.

In a further variant the catheter has in the distal region at least one temperature sensor which detects the temperature of the electrodes, the catheter and/or the surrounding tissue and feeds a corresponding temperature measurement value to a measurement value receiving device for further processing thereof.

Having regard to the preferred applications, the length of the shaft tube is between 600 and 2000 mm. A catheter of that kind is suitable for known applications for high-frequency therapy of hollow anatomical structures such as veins or bile ducts, but it is not restricted thereto, but in addition opens up new therapy procedures and areas of application. For therapy procedures of that kind it may be appropriate to know the extent to which the catheter has already been advanced in the hollow anatomical structures.

In accordance with a further variant the external peripheral surface of the shaft tube can accordingly be provided with spacing markings.

Endoluminal Use of the Catheter:

Firstly the guide wire is placed in the lumen of the hollow organ. Thereafter the high-frequency catheter is pushed over the guide wire while the guide wire remains in position, When the electrodes of the high-frequency catheter have reached the desired portion, a high-frequency ac voltage is applied to the electrodes. The position of the electrodes in the hollow organ can be altered by pushing the catheter forward and pulling it back, or by reciprocating movements.

In endoluminal use the hollow organ to be treated and possibly tumor tissue thereagainst have current flowing therethrough, they experience a rise in temperature and coagulate.

Treatment procedure on the example of varicose veins: A blood vessel to be treated is firstly preferably opened for example in the proximity of the ankle. A guide wire is then introduced under some circumstances by means of an endoscope into the opened vein. As the second step in the procedure the high-frequency catheter is introduced with its distal end leading into the opened vein over the guide wire and advanced as far as the end of the vein. In that case a high-frequency ac voltage which results in coagulation is not yet applied to the electrode or electrodes of the high-frequency catheter.

After the distal end of the high-frequency catheter is correctly positioned, a high-frequency ac voltage which causes shrinkage of the vein can be applied to the electrode provided for the treatment. In a monopolar arrangement the electrode intended for the treatment is arranged at the distal end of the high-frequency catheter. A counter-electrode is previously applied to the body of the patient in the form of a large-area neutral electrode. If in accordance with a preferred variant a bipolar high-frequency catheter is used the high-frequency ac voltage is applied between a proximally arranged and a distally arranged electrode.

In order to constrict the blood vessel over the desired length by coagulation the high-frequency catheter is then retracted slowly in the proximal direction relative to the guide wire or together with the guide wire. In that respect the speed of operation is adapted to the geometry of the blood vessel to be treated and to the applied high-frequency ac voltage. To increase the therapy effect, before application of the high-frequency ac voltage, the blood in the vein can be expelled over the entire length of the vein with a cuff.

In order to be able to approximately estimate the position of the electrode head at the distal end of the high-frequency catheter during the procedure, it is advantageous if a cord is so tensioned in parallel relationship with the high-frequency catheter from the connecting element of the application device, that the end of the cord or a marked location on the cord outside the body of the patient is approximately level with the electrode head within the patient. In that way the high-frequency catheter can be retracted in the proximal direction particularly sensitively and at a uniform speed. Further possible ways of checking the position are sonographic imaging, angiographic imaging, palpation or markings on the catheter shaft.

As soon as the elect odes leave the portion to be treated of a blood vessel, the electrodes are separated from the high-frequency ac voltage again and the high-frequency catheter can be entirely withdrawn from the body of the patient.

If the application device is connected to a corresponding control unit, the high-frequency ac voltage can be adapted to the respective demands involved, during the coagulation process. If the control unit is such that it delivers for example an acoustic or optical signal dependent on the impedance between the distal electrode and the counter-electrode, both the speed of withdrawal of the high-frequency catheter and also the magnitude of the high-frequency ac voltage can be particularly easily adapted to the respective requirements involved.

Treatment Procedure on the Example of the Fallopian Tube:

A further area of use of an application device with specific endoluminal involvement is constriction or sclerosis of a Fallopian tube for sterilization purposes. Firstly the guide wire and thereafter the high-frequency catheter are introduced by means of a hysteroscope (endoscope for gynaecology) from the uterus into the Fallopian tube to be closed off. The further procedure is the same as the constriction of veins (see above): after correct positioning of the electrode within the Fallopian tube high-frequency current is delivered and the electrode is withdrawn a defined distance so that the coagulated region contracts in respect of diameter and closes as a result.

Treatment Procedure on the Example of Tumors in the Region of the Bile Duct:

A further area of use of an application device with specific endoscopic involvement is the treatment of obstructive tumors in the region of the bile duct (ductus choledochus). Tumors in the region of the bile duct (for example cholangiocarcinoma) have the characteristic of compressing the bile duct, thereby causing partial or complete obstruction thereof.

To treat that indication the flexible endoscope (gastroscope or duodenoscope) is introduced through the buccal cavity, the esophagus and the stomach and positioned with the distal end in front of the major papilla of the duodenum. A guide wire is now introduced into the bile duct through the papilla and pushed beyond the portion of the bile duct which is to be treated. The high-frequency catheter is then advanced over the guide wire through the working passage of the endoscope until the electrode arrangement of the high-frequency catheter is in the region of the bile duct that is to be treated. By applying a high-frequency ac voltage to the electrodes the surrounding tissue (for example cholangiocarcinoma) is coagulated. Depending on the extent of the portion to be treated the coagulation operation is repeated at further locations. To remove the obstruction the electrode remains in the respective position until the individual coagulation operation is concluded. That results in the formation of a lumen of coagulated tissue of an inside diameter corresponding to the outside diameter of the electrode.

Then if necessary, at that location, a stent (a tubular element with which a lumen can be safeguarded against obstruction) can be fitted into the bile duct in order to prevent renewed obstruction by fibrin precipitation phenomena.

BRIEF DESCRIPTION OF THE DRAWINGS

The invention is described in greater detail hereinafter with reference to the drawings in which:

FIG. 1 is a perspective cross-sectional view showing a distal end piece of a catheter for the high-frequency therapy of biological tissue with a flexible shaft tube, an internal lumen extending therethrough, a plastic material hose which is drawn into the lumen of the shaft tube, a plastic tip, two ring electrodes, two electric lines and an insulator, FIG. 1a is a perspective view in partial cross-section showing a plastic material tube and a conical plastic material tip as constituent parts of the catheter of FIG. 1, shown separately, FIG. 1b is a perspective cross-sectional view showing a flexible shaft tube as a constituent part of the catheter of FIG. 1, shown separately, FIG. 1c is a perspective cross-sectional view showing electrodes and electric lines of the catheter of FIG. 1, shown separately, FIG. 1d is a perspective cross-sectional view showing an insulator arranged between the electrodes as a constituent part of the catheter of FIG. 1, shown separately, FIG. 2 is a side elevational view of the distal end piece of a catheter in accordance with a second embodiment of the invention, FIG. 2A is a cross-sectional view taken along the A-A line of FIG. 2 of the distal end piece of a catheter in accordance with a second embodiment with the flexible shaft tube, an internal lumen extending therethrough, a distal end piece which is divided into two, two ring electrodes and an insulator.

DETAILED DESCRIPTION OF THE INVENTION

Figure 3:
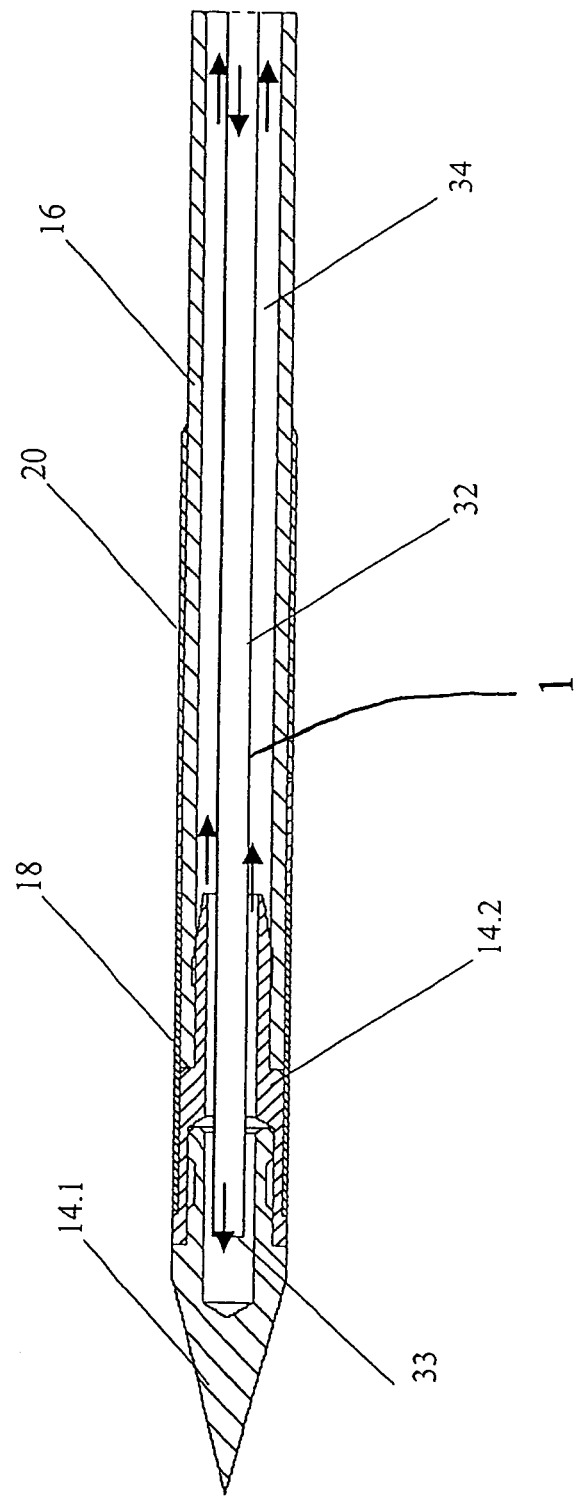
FIG. 3 is a cross-sectional view of the distal end piece of a catheter in accordance with a third embodiment with a flexible shaft tube, an internal lumen which is closed at its distal end, a distal end piece which is divided into two and a cooling system.

Referring to FIGS. 1 through 1d, a distal end piece of the high-frequency catheter according to the invention is shown in a particularly preferred embodiment; comprising a lumen 1 extending therethrough for passing a guide wire therethrough; in a bipolar variant.

The lumen is of a diameter of 0.81 mm and is suitable for receiving a guide wire of a diameter of 0.025 inch. In an alternative variant (not shown) the lumen 1 can also be of a larger diameter which is suitable for receiving a guide wire of a diameter of 0.035 inch.

The distal end of the catheter has a distal end piece 14. A distal part 14.d of the end piece 14 is in the form of a plastic material tip, while a cylindrical proximal part 14.p of the end piece 14, which projects into the distal end of a flexible shaft tube 16, forms a clamping connection to the distal end of the flexible shaft tube 16.

The end piece 14 has a central bore which opens into the lumen 1 which extends as far as the proximal end of the catheter. The external peripheral surface of the distal part 14.d, which is in the form of a frustoconical plastic tip, of the distal end piece 14 extends at an angle of 15 degrees as measured between the conical peripheral surface and a line parallel to the axis of the catheter, wherein the outside diameter of the plastic material tip goes steplessly into the outside diameter of a distal ring electrode 18. At the transition between the distal part 14.d and the proximal part 14.p of the distal end piecedistal end piece 14 therefore the outside diameter of the distal part 14.d which is in the form of the plastic tip corresponds to the outside diameter of the distal ring electrode 18.

In the variant illustrated here, besides the distal ring electrode 18, a proximal ring electrode 20 is drawn on to the shaft tube 16 of the catheter. The two ring electrodes 18, 20 are preferably formed from a biocompatible high-quality steel. In this embodiment, the distal ring electrode 18 has the function of a sleeve which secures the clamping connection between the shaft tube 16 and the proximal part 14.p of the end piece 14 insofar as it exerts a radially inwardly directed damping force on the part of the shaft tube 16 enclosed thereby, and thereby increases the clamping force between the shaft tube 16 and the distal end piece 14.

It is not possible to see from FIG. 1 that the proximal part 14.p of the end piece 14 can have a variation in cross-section of the outer diameter, for example in the form of a projection which circumferentially extends in a ring shape and which hinders an axial displacement of the end piece 14 within the shaft tube 16 and thus guarantees an even stronger hold for the distal electrode 18 on the shaft tube 16.

The flexible shaft tube 16 is preferably formed from polyetheretherketone (PEEK).

Arranged in the axial direction between the two electrodes 18 and 20 is an insulator 26 which with its longitudinal ends directly adjoins a respective one of the two electrodes 18 and 20 and which, like the electrodes 18 and 20, is also pulled on to the shaft tube 16 of the catheter on the outside thereof. The insulator 26 is preferably formed from PEEK. The electrodes 18 and 20 as well as the insulator 26 are of the same outside diameter of 2.0 mm and preferably also an identical inside diameter of 1.8 mm.

The distal electrode 18 is preferably at a spacing of 1.8 mm relative to the distal end of the catheter and a length measured in the longitudinal direction of the catheter of about 5.4 mm. The insulator 26 is of a length which constitutes approximately 10% of the active part, which is preferably 12 mm long, consisting of the distal electrode 18+insulator 26+proximal electrode 20, and which is thus 1.2 mm. The proximal electrode is preferably of the same length as the distal electrode 18.

Two electric lines 22 and 24 are connected preferably by clamping contacting to the distal and proximal electrodes 18 and 20. The two lines 22 and 24 preferably comprise copper and are each of a diameter of preferably 0.15 mm. They are passed through the two passages 28 and 30 of the shaft tube 16 and extend from the distal and proximal electrodes 18 and 20 respectively along the internal peripheral surface of the shaft tube 16 to the proximal end (not visible) of the catheter where they are connected to a plug or adaptor for connection to a high-frequency generator.

The passages 28 and 30 are preferably disposed on respective opposite sides of the shaft tube 16.

For insulating the lines 22 and 24 and for fixing them to the internal peripheral surface of the shaft tube 16, a plastic material hose 12 is drawn into the lumen 1 of the shaft tube 16. The hose 12 extends from the proximal end (not visible) of the catheter to the junction between the proximal part 14.p and the distal part 14.d of the end piece 14.

Consequently, the lines 22 and 24 extend between the passages 28 and 30 and the proximal end of the catheter in an intermediate space between the shaft tube 16 and an internal plastic tube 12.

In this embodiment, the diameter of the catheter lumen 1 corresponds to the inside diameter 1 of the plastic hose.

FIGS. 1a through 1d show the catheter of FIG. 1, illustrated separately. FIG. 1a shows the plastic hose 12 with the distal part 14.d of the end piece 14, the part 14.d being in the form of a plastic material tip. It can be seen at the distal end of the plastic tip that the entry to the central bore is of a funnel-shaped configuration, wherein the internal peripheral surface at that location extends at an angle of about 45 degrees as measured between the conical internal peripheral surface and a line parallel to the axis of the catheter. That funnel-shaped configuration makes it easier to receive a guide wire.

The plastic hose 12 is advanced as far as the junction between the proximal part 14.p and the distal part 14.d of the end piece 14 in the central bore of the end piece 14. In this variant the plastic hose 12 and the end piece 14 can be joined together by way of a press fit or also by a welded connection or an adhesive connection.

FIG. 1b shows a view in section of the flexible shaft tube 16. It is possible to clearly see therein the two passages 28 and 30 for the lines 22 and 24.

FIG. 1c shows a sectional view of the distal electrode 18 and the proximal electrode 20 with the associated electric lines 22 and 24. The electric lines 22 and 24 extend from the proximal end of the catheter to the respective passages 28 and 30 provided for same, parallel to the longitudinal axis of the catheter. After having passed through the respective passage in the periphery of the shaft tube 16, for which purpose they have a first bend through 90 degrees corresponding to the radial orientation of the passages 28 and 30, they also extend after having passed through the peripheral surface of the shaft tube 16 preferably in the axial-distal or axial-proximal direction, and correspondingly have a second bend through 90 degrees. By virtue of the ring electrodes 18 and 20 being drawn on to the shaft tube 16 the lines 22 and 24 are clamped by the radially inwardly acting clamping force of the electrodes 18 and 20 between the respective electrode 18 or 20 and the shaft tube 16, thereby providing the clamping contacting action between the lines 22 and 24 and the electrodes 18 and 20. In alternative variants the connection between the lines and the respective electrode can be made additionally or exclusively by a join involving intimate bonding of the materials concerned, such as for example adhesive or soldering.

FIG. 1d shows a view in section of the insulator 26.

FIGS. 2 and 2A show a distal portion 10 of the high-frequency catheter according to the invention in a further variant, comprising a through lumen 1 for passing a guide wire therethrough; in a bipolar variant.

The difference in relation to the variant shown in FIG. 1 is in particular that the distal end piece 14 is divided into two and comprises a distal sub-piece 14.1 and a proximal sub-piece 14.2.

A proximal cylindrical part 14.p of the proximal sub-piece 14.2 projects in this case into the distal end of the shaft tube 16 and forms a clamping connection with the distal end of the flexible shaft tube 16. As was not shown in FIG. 1, this illustration shows a variation in cross-section on the external peripheral surface of the proximal part 14.p of the proximal sub-piece 14.2. As already described that variation in cross-section enhances the load-bearing capability of the clamping connection and hinders axial movement of the proximal sub-piece 14.2.

The proximal sub-piece 14.2 is preferably made from metal in order to be able to carry a greater radial force acting due to the sleeve or the distal ring electrode 18 and to increase the load-bearing capability of the clamping connection.

At the location at which the proximal sub-piece 14.2 projects out of the shaft tube 16, the outside diameter of the sub-piece 14.2 is enlarged to the outside diameter of the shaft portion 16 and fixes the sub-piece 14.2 in relation to a distally directed axial movement.

A further cross-sectional enlargement of the outside diameter of the proximal sub-piece 14.2 to the outside diameter of the distal ring electrode 18 forms a flange at the distal end of the proximal sub-piece 14.2 and prevents axial displacement of the distal ring electrode 18 in the distal direction.

In order to connect the distal sub-piece 14.1 to the proximal sub-piece 14.2 a distal part 14.z of the proximal sub-piece 14.2 encloses the proximal part 14.z of the distal sub-piece 14.1. Provided on the external peripheral surface of the distal sub-piece 14.1, in a proximal part 14.z, are cross-sectional changes which are compatible with the cross-sectional changes of the internal peripheral surface of the proximal sub-piece 14.2 in a distal part 14.z and thus permit a latching connection between the two sub-pieces 14.1 and 14.2. In this variant the clamping or latching connection is also secured by the distal ring electrode 18 which secures both connections by the radially acting force on the parts 14.z and 14.p.

In this variant also the distal sub-piece 14.1 has a distal part which is in the form of a tip and is preferably made from plastic material. The variant of the distal end piece 14 with two sub-pieces 14.1 and 14.2, described with reference to FIGS. 2 and 2A, has the advantage over the variant described with reference to FIG. 1 that the two sub-pieces 14.1 and 14.2 of the distal end piece 14 can be formed from different materials.

FIG. 3 shows a cross-sectional view of the distal end of a third embodiment of the catheter.

As in all embodiments of the catheter this embodiment also has a flexible shaft tube 16 enclosing a lumen 1. Unlike the situation with the first two embodiments the lumen 1 of the catheter illustrated here is closed at the distal end.

As also in the second embodiment, the diameter of the lumen 1 in the embodiment illustrated here goes from the inside diameter of the flexible shaft tube 16 into the inside diameter of a distal end piece which is divided into two distal sub-pieces 14.1, 14.2. The proximal part of the distal end piece 14.2 in this arrangement has a through bore. Unlike the embodiments shown hitherto, the distal sub-piece 14.1 of the two sub-piece end piece however has a blind bore. Accordingly, in contrast to the embodiments 1 and 2, the lumen of the catheter ends in the blind bore of the distal sub-piece 14.1 of the two sub-pieces of the end piece. The internal space in the catheter is therefore enclosed so that no fluid can pass from the interior of the catheter outwardly or vice-versa.

The catheter shown in FIG. 3 also has a cooling system with a proximal feed and discharge flow (not shown here) for a cooling medium. In this case the cooling system shown here is formed by a feed conduit 32 which is held only at the proximal end (not shown) of the catheter and the distal end of which can move relatively freely in the distal end of the catheter and, as shown here, in the bore in the distal end sub-pieces 14.1, 14.2. Like the shaft tube 16 the feed conduit 32 is made from a flexible plastic material, for example PEEK. In this case a catheter in this embodiment can be flushed with a cooling fluid. For that purpose a cooling medium is fed to the feed conduit 32 by way of a proximal feed flow means, the cooling medium issuing from a distal mouth opening 33 of the feed conduit 32 and in so doing cooling in particular the distal end of the catheter. By virtue of the closed distal shaft end the cooling medium thereupon flows back through an intermediate space 34 between the outside diameter of the feed conduit 32 and the inside diameter of the flexible shaft tube 16 to the proximal end of the shaft where it issues from the catheter at the proximal discharge flow means.

Figure 4:
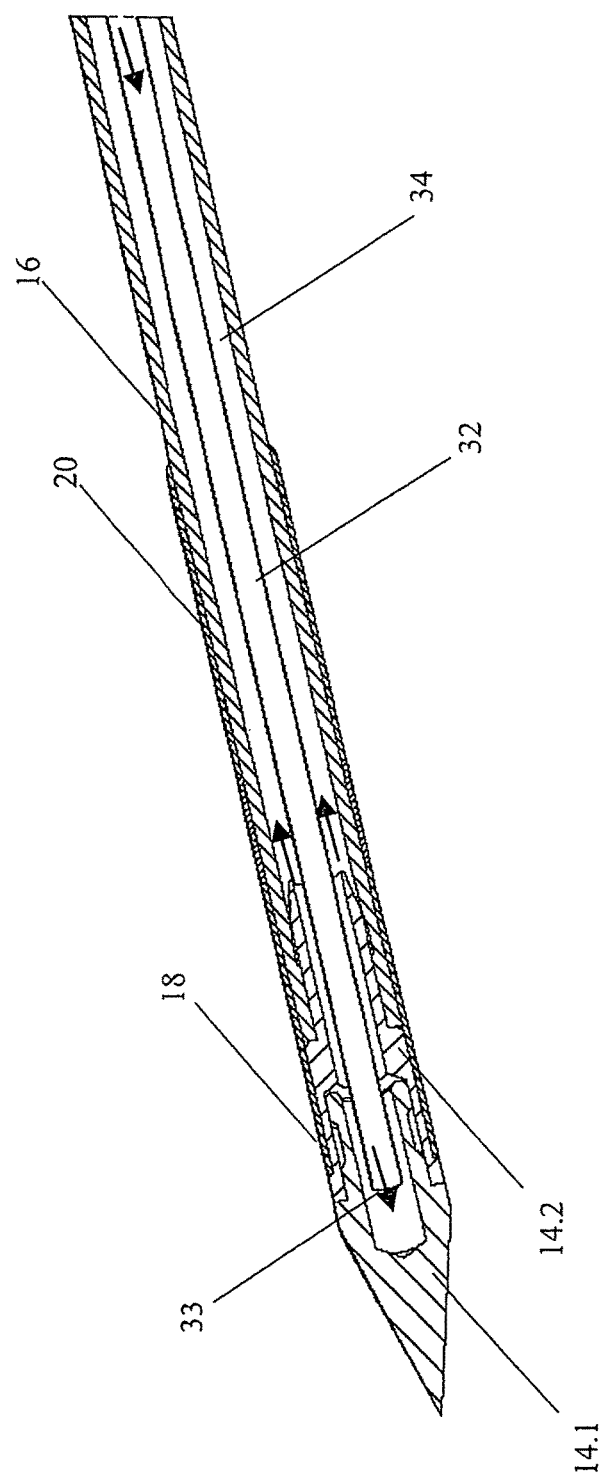
FIG. 4 is a perspective cross-sectional view of the embodiment of the catheter shown in FIG. 3.

FIG. 4 is a perspective view of the embodiment of the catheter shown in FIG. 3. The description of FIG. 3 can thus be completely carried over on to FIG. 4.

The invention claimed is:

1. A catheter for the treatment of body tissue comprising:
a flexible shaft tube of biocompatible plastic material, which defines a lumen,
a distal end piece fixed to a distal end of the flexible shaft tube, a proximal end of the distal end piece projects into the lumen of the flexible shaft tube and there forms a clamping connection to the distal end of the flexible shaft tube, wherein the distal end piece is divided into a proximal sub-piece having at least one change in outside diameter and a distal sub-piece, wherein the proximal end of the distal end piece is part of the proximal sub-piece, and the distal sub-piece is connected to the proximal sub-piece by a distal part of the proximal sub-piece enclosing a proximal part of the distal sub-piece,
at least one electrode on a distal portion of the flexible shaft tube adapted to deliver high-frequency alternating current to body tissue surrounding the catheter during treatment, wherein the distal portion of the flexible shaft tube comprises the distal end of the flexible shaft tube, wherein said at least one electrode includes a sleeve in the form of a hollow cylinder which exerts a radially acting clamping force on the clamping connection, and
at least one electric line which is electrically conductingly connected to the at least one electrode and which extends to a proximal end of the catheter.

2. A catheter as set forth in claim 1, wherein the sleeve is electrically conducting and forms the at least one electrode on the distal portion of the flexible shaft tube.

3. A catheter as set forth in claim 1, wherein the proximal sub-piece is electrically conducting.

4. A catheter as set forth in claim 1, wherein the distal sub-piece of the distal end piece has at least one change in outside diameter.

5. A catheter as set forth in claim 1, wherein the sleeve has at least one change in inside diameter.

6. A catheter as set forth in claim 1, wherein the proximal part of the distal sub-piece projects into the distal part of the proximal sub-piece and wherein the distal sub-piece is connected to the proximal sub-piece by a force-locking connection, a positively locking connection or a joint involving intimate bonding thereof.

7. A catheter as set forth in claim 6, wherein the sleeve at least in part encloses the proximal sub-piece and the distal sub-piece of the distal end piece where the distal part of the proximal sub-piece encloses the proximal part of the distal sub-piece.

8. A catheter as set forth in claim 1, wherein the distal end piece forms a tip at a distal end of the catheter.

9. A catheter as set forth in claim 8, wherein the tip comprises polyphenylsulfone (PPSU) or polyetheretherketone (PEEK).

10. A catheter as set forth in claim 8, wherein the tip is provided with an anti-adhesion coating.

11. A catheter as set forth in claim 8, wherein the tip has a conical, trocar-shaped, cylindrical or spherical end face.

12. A catheter as set forth in claim 8, wherein the tip has an outside diameter matching an outside diameter of the flexible shaft tube and tapers downward at an angle of between 10° and 20° in a longitudinal direction of the catheter towards the distal end of the catheter.

13. A catheter as set forth in claim 1, further including a plastic hose in the lumen of the flexible shaft tube.

14. A catheter as set forth in claim 13, wherein the plastic hose and the flexible shaft tube comprise an electrically insulating material.

15. A catheter as set forth in claim 13, wherein the plastic hose comprises polyimide (PI).

16. A catheter as set forth in claim 13, wherein the flexible shaft tube is fluid-tightly connected to the plastic hose by welding, adhesive or by a press connection.

17. A catheter as set forth in claim 1, wherein the lumen is of a diameter of between 0.65 mm and 1.6 mm.

18. A catheter as set forth in claim 1, wherein the flexible shaft tube comprises polyetheretherketone (PEEK).

19. A catheter as set forth in claim 1, wherein the flexible shaft tube has at least one passage for passing the at least one electric line therethrough.

20. A catheter as set forth in claim 1, wherein the at least one electrode including the sleeve comprise at least two ring electrodes on the flexible shaft tube.

21. A catheter as set forth in claim 20, further including an annular insulator between the at least two ring electrodes.

22. A catheter as set forth in claim 21, wherein the annular insulator comprises polyetheretherketone (PEEK).

23. A catheter as set forth in claim 1, wherein the flexible shaft tube has a length between 600 and 2000 mm.

24. A catheter as set forth in claim 1, wherein the flexible shaft tube of the catheter has an outside diameter less than or equal to 5 mm.

25. A catheter as set forth in claim 1, further including a temperature sensor at a distal end of the catheter for detecting tissue temperature in proximity of the catheter or catheter temperature.

26. A catheter as set forth in claim 1, wherein the distal end piece has a central axial through bore forming a distal mouth opening.

27. A catheter as set forth in claim 26, wherein the distal mouth opening has a diameter of between 0.65 and 2 mm.

28. A catheter as set forth in claim 1, wherein the lumen is continuous between the proximal and distal ends of the catheter and the catheter has proximal and distal mouth openings, so that a guide wire can be introduced by way of the proximal mouth opening, advanced to the distal end through the lumen and issue again through the distal mouth opening.

29. A catheter as set forth in claim 1, wherein the distal end piece has a frustoconical configuration tapering at an angle of between 15 and 85 degrees.

30. A catheter as set forth in claim 1, wherein the catheter is closed at a distal end.

31. A catheter as set forth in claim 30, further including a cooling system with a proximal feed and discharge flow means for a cooling medium in the catheter.

32. A method for electrosurgical treatment of body tissue in the lumen of a hollow organ, including the steps of:
a) providing a catheter comprising:
a flexible shaft tube of biocompatible plastic material, which defines a lumen,
a distal end piece fixed to a distal end of the flexible shaft tube, a proximal end of the distal end piece projects into the lumen of the flexible shaft tube and there forms a clamping connection to the distal end of the flexible shaft tube, wherein the distal end piece is divided into a proximal sub-piece having at least one change in outside diameter and a distal sub-piece, wherein the proximal end of the distal end piece is part of the proximal sub-piece, and the distal sub-piece is connected to the proximal sub-piece by a distal part of the proximal sub-piece enclosing a proximal part of the distal sub-piece, at least one electrode on a distal portion of the flexible shaft tube adapted to deliver high-frequency alternating current to body tissue surrounding the catheter during treatment, wherein the distal portion of the flexible shaft tube comprises the distal end of the flexible shaft tube, wherein said at least one electrode includes a sleeve in the form of a hollow cylinder which exerts a radially acting clamping force on the clamping connection, and at least one electric line which is electrically conductingly connected to the at least one electrode and which extends to a proximal end of the catheter;

b) placing a guide wire in the lumen of the hollow organ;
c) pushing the catheter over the guide wire, while the guide wire remains in position;
d) advancing the catheter until the at least one electrode has reached a desired position; and
e) applying high-frequency AC voltage to the at least one electrode thereby delivering the high frequency alternating current to the body tissue surrounding the catheter during treatment.

33. A method for electrosurgical treatment of varicose veins, including the steps of:
a) providing a catheter comprising:
a flexible shaft tube of biocompatible plastic material, which defines a lumen,
a distal end piece fixed to a distal end of the flexible shaft tube, a proximal end of the distal end piece projects into the lumen of the flexible shaft tube and there forms a clamping connection to the distal end of the flexible shaft tube, wherein the distal end piece is divided into a proximal sub-piece having at least one change in outside diameter and a distal sub-piece, wherein the proximal end of the distal end piece is part of the proximal sub-piece, and the distal sub-piece is connected to the proximal sub-piece by a distal part of the proximal sub-piece enclosing a proximal part of the distal sub-piece,
at least one electrode on a distal portion of the flexible shaft tube adapted to deliver high-frequency alternating current to body tissue surrounding the catheter during treatment, wherein the distal portion of the flexible shaft tube comprises the distal end of the flexible shaft tube, wherein said at least one electrode includes a sleeve in the form of a hollow cylinder which exerts a radially acting clamping force on the clamping connection, and
at least one electric line which is electrically conductingly connected to the at least one electrode and which extends to a proximal end of the catheter;
b) opening a desired blood vein to create an opened vein;
c) introducing a guide wire into the opened vein;
d) pushing the catheter over the guide wire, introducing the catheter into the opened vein and advancing the catheter as far as the end of the opened vein;
e) providing a high-frequency AC voltage to the at least one electrode when the distal end of the catheter is correctly positioned thereby delivering the high frequency alternating current to the body tissue surrounding the catheter during treatment; and
f) retracting the catheter slowly in a proximal direction relative to the guide wire or together with the guide wire with a speed that is adapted to the geometry of the opened vein being treated and to the high-frequency AC voltage.

34. The method according to claim 33, whereby, before applying the high-frequency AC voltage to the at least one electrode, the method further comprising the step of expelling any blood within the opened vein using a cuff.

35. The method according to claim 33, whereby a cord is tensioned in parallel relationship with the catheter from a connecting element so that an end of the cord or a marked location on the cord outside the opened vein is approximately level with the at least one electrode within the opened vein.

36. The method according to claim 33, wherein speed of withdrawal of the catheter, the high-frequency AC voltage, or both are chosen depending on impedance between the at least one electrode and a counter-electrode.

37. A method for constriction or sclerosis of a fallopian tube, including the steps of:
a) providing a catheter comprising:
a flexible shaft tube of biocompatible plastic material, which defines a lumen,
a distal end piece fixed to a distal end of the flexible shaft tube, a proximal end of the distal end piece projects into the lumen of the flexible shaft tube and there forms a clamping connection to the distal end of the flexible shaft tube, wherein the distal end piece is divided into a proximal sub-piece having at least one change in outside diameter and a distal sub-piece, wherein the proximal end of the distal end piece is part of the proximal sub-piece, and the distal sub-piece is connected to the proximal sub-piece by a distal part of the proximal sub-piece enclosing a proximal part of the distal sub-piece,
at least one electrode on a distal end of the flexible shaft tube adapted to deliver high-frequency alternating current to body tissue surrounding the catheter during treatment, wherein the distal portion of the flexible shaft tube comprises the distal end of the flexible shaft tube, wherein said at least one electrode includes a sleeve in the form of a hollow cylinder which exerts a radially acting clamping force on the clamping connection, and
at least one electric line which is electrically conductingly connected to the at least one electrode and which extends to a proximal end of the catheter;
b) introducing a guide wire and thereafter the catheter by means of a hysteroscope or an endoscope from a uterus into the fallopian tube to be closed off;
c) advancing the catheter as far as the end of the fallopian tube;
d) providing a high-frequency AC voltage to the at least one electrode when a distal end of the catheter is correctly positioned thereby delivering the high frequency alternating current to the body tissue surrounding the catheter during treatment; and
e) withdrawing the catheter while delivering a high-frequency current within a defined distance so that a desired region contracts in respect of diameter and closes as a result.

38. A method for treating obstructive tumors in the region of the bile duct (ductus choledochus) in a patient, including the steps of:
a) providing a catheter comprising:
a flexible shaft tube of biocompatible plastic material, which defines a lumen,
a distal end piece fixed to a distal end of the flexible shaft tube, a proximal end of the distal end piece projects into the lumen of the flexible shaft tube and there forms a clamping connection to the distal end of the flexible shaft tube, wherein the distal end piece is divided into a proximal sub-piece having at least one change in outside diameter and a distal sub-piece, wherein the proximal end of the distal end piece is part of the proximal sub-piece, and the distal sub-piece is connected to the proximal sub-piece by a distal part of the proximal sub-piece enclosing a proximal part of the distal sub-piece, at least one electrode on a distal portion of the flexible shaft tube adapted to deliver high-frequency alternating current to body tissue surrounding the catheter during treatment, wherein the distal portion of the flexible shaft tube comprises the distal end of the flexible shaft tube, wherein said at least one electrode includes a sleeve in the form of a hollow cylinder which exerts a radially acting clamping force on the clamping connection, and at least one electric line which is electrically conductingly connected to the at least one electrode and which extends to a proximal end of the catheter;

b) introducing a flexible endoscope, gastroscope or duodenoscope through the patient, and positioning a distal end of the endoscope, gastroscope or duodenoscope in front of papilla of the duodenum;

c) introducing a guide wire into the bile duct and advancing the guide wire beyond a portion of the bile duct which is to be treated, d) advancing the catheter over the guide wire until the at least one electrode of the catheter is within the portion of the bile duct that is to be treated; and e) applying a high-frequency AC voltage to the at least one electrode thereby delivering the high frequency alternating current to the body tissue surrounding the catheter during treatment and thereby coagulating the body tissue surrounding the catheter during treatment.

39. The method according to claim 38, further including a step of fitting a stent into the bile duct in order to prevent renewed obstruction by fibrin precipitation phenomena.

* * * * *